US010429344B2

United States Patent
Daecke et al.

(10) Patent No.: US 10,429,344 B2
(45) Date of Patent: Oct. 1, 2019

(54) METHOD AND DEVICE FOR DETECTING AT LEAST A PORTION OF THE MEASURING GAS COMPONENT CONTAINING BOUND OXYGEN IN A GAS MIXTURE

(71) Applicant: Robert Bosch GmbH, Stuttgart (DE)

(72) Inventors: Dirk Daecke, Stuttgart (DE); Jan Dominique Makowski, Stuttgart (DE); Moritz Waldorf, Stuttgart (DE); Reinhard Hein, Sachsenheim (DE); Andreas Dreyer, Ditzingen (DE); Peter Oechtering, Karlsruhe (DE)

(73) Assignee: Robert Bosch GmbH, Stuttgart (DE)

( * ) Notice: Subject to any disclaimer, the term of this patent is extended or adjusted under 35 U.S.C. 154(b) by 336 days.

(21) Appl. No.: 15/510,711

(22) PCT Filed: Sep. 1, 2015

(86) PCT No.: PCT/EP2015/069939
§ 371 (c)(1),
(2) Date: Mar. 13, 2017

(87) PCT Pub. No.: WO2016/037900
PCT Pub. Date: Mar. 17, 2016

(65) Prior Publication Data
US 2017/0284959 A1 Oct. 5, 2017

(30) Foreign Application Priority Data

Sep. 11, 2014 (DE) .......... 10 2014 218 223
Jun. 9, 2015 (DE) .......... 10 2015 210 473

(51) Int. Cl.
*G01N 27/417* (2006.01)
*G01N 27/41* (2006.01)
*G01N 27/419* (2006.01)

(52) U.S. Cl.
CPC .......... *G01N 27/419* (2013.01); *G01N 27/41* (2013.01); *G01N 27/417* (2013.01)

(58) Field of Classification Search
CPC .. G01N 27/407; G01N 27/4071; G01N 27/41; G01N 33/0037; G01N 33/004; G01N 33/0042
See application file for complete search history.

(56) References Cited

U.S. PATENT DOCUMENTS

| 2002/0162743 A1* | 11/2002 | Inagaki | G01N 27/4065 204/425 |
| 2005/0288847 A1 | 12/2005 | Inoue et al. | |
| 2011/0036715 A1* | 2/2011 | Horisaka | G01N 27/4071 204/424 |

FOREIGN PATENT DOCUMENTS

| CN | 101910833 A | 12/2010 |
| CN | 201666193 U | 12/2010 |

(Continued)

OTHER PUBLICATIONS

EPO computer-generated English language translation of DE 1020029027 A1. Downloaded Apr. 18, 2019. Patent published Nov. 17, 2011. (Year: 2011).*
EPO computer-generated English language translation, downloaded 06/145/2019, of the Description section of DE 102009047359 A1, patented Jun. 9, 2011. (Year: 2011).*
International Search Report dated Nov. 19, 2015, of the corresponding International Application PCT/EP2015/069939 filed Sep. 1, 2015.

*Primary Examiner* — Alexander S Noguerola
(74) *Attorney, Agent, or Firm* — Norton Rose Fulbright US LLP; Gerard Messina

(57) ABSTRACT

A method and a device are described for detecting at least a portion of a measuring gas component containing bound oxygen in a gas mixture, in particular in an exhaust gas of an internal combustion engine, in a measuring gas chamber by detecting a portion of oxygen that is generated by a reduction of the measuring gas component containing the bound oxygen, in the presence of molecular oxygen, in the device, which includes at least one first pump cell, one (Continued)

reference cell, and one second pump cell. The method includes the following steps: a) generating a first pump current in the first pump cell in such a way that transport of a first portion of oxygen ions takes place between the measuring gas chamber and the surroundings of the device; b) applying a reference pump current to the reference cell in such a way that a second portion of the oxygen ions is transported into a reference gas chamber; c) decomposing the measuring gas component containing the bound oxygen by catalysis at an electrode of the second pump cell, as the result of which additional molecular oxygen is generated from the measuring gas component; d) applying a second pump current to the second pump cell in such a way that a portion of further oxygen ions that are formed from the additional molecular oxygen is transported into the reference gas chamber; and e) holding a sum of currents, formed from the reference pump current and from the second pump current, constant.

15 Claims, 10 Drawing Sheets

(56) References Cited

FOREIGN PATENT DOCUMENTS

| | | |
|---|---|---|
| DE | 102009047359 A1 | 6/2011 |
| DE | 102010029027 A1 | 11/2011 |
| EP | 0769693 A1 | 4/1997 |
| JP | H09509747 A | 9/1997 |
| JP | 2010249801 A | 11/2010 |
| WO | 2008154366 A2 | 12/2008 |

* cited by examiner

METHOD AND DEVICE FOR DETECTING AT LEAST A PORTION OF THE MEASURING GAS COMPONENT CONTAINING BOUND OXYGEN IN A GAS MIXTURE

FIELD OF THE INVENTION

The present invention relates to a method and a device for detecting at least a portion of a measuring gas component containing bound oxygen in a gas mixture, in particular in an exhaust gas of an internal combustion engine, in a measuring gas chamber by detecting a portion of oxygen that is generated by a reduction of the measuring gas component containing the bound oxygen, in the presence of molecular oxygen. Moreover, the present invention relates to a computer program which is configured for carrying out the steps of this method, an electronic memory medium on which a computer program of this type is stored, and an electronic control unit which includes in particular an electronic memory medium of this type.

BACKGROUND INFORMATION

Methods and devices for detecting at least a portion of a gas in a gas mixture are known from the related art. The present invention is described below, without limitation of further possible embodiments, essentially with reference to devices that are used for quantitatively and/or qualitatively detecting at least a portion in particular of a partial pressure and/or a volume portion and/or mass portion, of a gas in a gas mixture. For example, the gas may be an exhaust gas of an internal combustion engine, in particular in the automotive field. The sensor for detecting the gas portion is in particular a lambda sensor. Lambda sensors are described, for example, in Konrad Reif, Ed., Sensoren im Kraftfahrzeug [Automotive Sensors], 2nd Edition, 2012, pp. 160-165. Lambda sensors, in particular universal lambda sensors, place two mass flows, in particular oxygen mass flows, between two spaces, which may be a gas chamber outside the device or a cavity in the device, into an equilibrium. One of the mass flows is driven across a diffusion barrier due to concentration differences. Another mass flow is driven across a solid-state electrolyte and two electrodes, in particular two pump electrodes, controlled by an applied pump current. The pump current is preferably adjusted in such a way that a constant, very low oxygen concentration results in the cavity. A concentration profile across the diffusion barrier is uniquely determined by a constant control point in the cavity, in particular a constant setpoint voltage that results in an oxygen concentration, and by an oxygen concentration on the exhaust gas side. An inflow of oxygen molecules from the measuring gas chamber to the cavity results, corresponding to this unique concentration profile, and corresponds to the adjusted pump current. Therefore, the pump current may be used as a measured value of the oxygen concentration in the measuring gas chamber, in particular the oxygen concentration present on the exhaust gas side.

Furthermore, methods and devices are known for detecting at least a portion of the measuring gas component containing bound oxygen in a gas mixture, in particular in an exhaust gas of an internal combustion engine, by detecting a portion of oxygen that is generated by a reduction of the measuring gas component containing the bound oxygen, in the presence of molecular oxygen. European Published Patent Application No. 0769693 provides a method and a device for detecting at least a portion of the measuring gas component containing bound oxygen, in particular nitrogen oxides $NO_x$, in a gas mixture by detecting a portion of oxygen that is generated by a reduction of the measuring gas component containing the bound oxygen, in the presence of molecular oxygen, in particular by the reduction of the nitrogen oxides $NO_x$ with the aid of a catalyst that is suitable for this purpose. The device described therein includes a first pump cell which adjoins a first cavity that is connected to the measuring gas chamber, the first pump cell being used for transporting oxygen from the first cavity, resulting in a lower oxygen partial pressure in the first cavity. The device also includes a reference cell which adjoins a reference gas chamber and is used for transporting oxygen from the second cavity in such a way that an oxygen partial pressure in an atmosphere in the second cavity may be regulated in such a way that the oxygen partial pressure has a value which essentially does not adversely affect the detection of the portion of the measuring gas component. Lastly, the device includes a second pump cell which adjoins a second cavity, whereby an electrode which adjoins the second cavity, in particular due to a catalyst introduced into the electrode for this purpose, is configured for reducing or decomposing the measuring gas component containing the bound oxygen, preferably nitrogen oxides $NO_x$, in the atmosphere introduced into the second cavity. The oxygen which is generated by reduction or decomposition of the measuring gas component in the second cavity, and which preferably originates from the reduction of the nitrogen oxides $NO_x$, is transported into the reference gas chamber with the aid of the second pump current, and its proportion is detected using a value to which the second pump current is set. The portion of nitrogen oxides $NO_x$ in a gas mixture, which in addition to the nitrogen oxides $NO_x$ also includes oxygen, in a measuring gas chamber may be determined in the described manner with the aid of a cascade of at least three pump cells situated in succession.

Devices for on-board diagnostics (OBD) of motor vehicles are also known from the related art. By use of OBD, in particular components of an internal combustion engine in a motor vehicle that have an influence on a characteristic of an exhaust gas of the internal combustion engine may be monitored. With regard to a characteristic of the exhaust gas, faults that occur are detected by the OBD and indicated to the driver of the motor vehicle via an indicator light, for example, and permanently stored in an associated control unit. OBD was first introduced in 1988 by the California Air Resources Board (CARB) against the background that compliance with the exhaust gas emission limits should be ensured not only at licensing of the motor vehicle, but also over its service life. In the further development of the second generation of the vehicle onboard electronics systems for self-monitoring (CARB OBD II) presently in use, there are requirements, inter alia,—in contrast to known electronic control devices—for accurately determining and locating malfunctions of the exhaust gas-relevant systems, for which the term "pinpointing" is also used.

In this regard, variations in output currents from current sources, which may have tolerances of up to 30% or greater, play a special role. As the result of manufacturing-related tolerances of the components used for the current sources, together with additional effects, in particular due to aging of the components and/or due to temperatures to which the components are exposed, the output currents of the current sources may differ significantly from their nominal values. However, as discussed above, since the oxygen partial pressure in the reference cell is proportional to the magnitude of the reference pump current, the resulting variations in the reference pump current may have quite major effects on the characteristics and functioning of the devices for detecting at least a portion of a measuring gas component in a measuring gas chamber. If the reference pump current differs from an established setpoint value in this way, the measuring accuracy of the known sensors for detecting the gas portion may be greatly limited.

SUMMARY

The present invention provides a method and a device for detecting at least a portion of a measuring gas component containing bound oxygen in a gas mixture, in particular in an exhaust gas of an internal combustion engine, in a measuring gas chamber by detecting a portion of oxygen that is generated by a reduction of the measuring gas component containing the bound oxygen, in the presence of molecular oxygen, in a device which includes at least one first pump cell, one reference cell, and one second pump cell, a computer program which is configured for carrying out the steps of this method, an electronic memory medium on which this type of computer program is stored, and an electronic control unit which in particular includes this type of electronic memory medium, via which the disadvantages of such methods and devices known from the related art may be at least partially avoided.

The present invention is based on the fact that detecting the portion of the measuring gas component containing bound oxygen, in particular chemically bound oxygen, preferably nitrogen oxides $NO_x$, sulfur oxides $SO_x$, and/or carbon oxides $CO_x$, according to the related art is based on the assumption that the portion of oxygen contained in the reference gas chamber originates preferably entirely from the reduction of the measuring gas component to be detected, in particular the nitrogen oxides $NO_x$, sulfur oxides $SO_x$, and/or carbon oxides $CO_x$. Based on this assumption, it is accordingly assumed that the value to which the second pump current is set is thus proportional to the portion of the measuring gas component to be detected, in particular the nitrogen oxides $NO_x$, sulfur oxides $SO_x$, and/or carbon oxides $CO_x$. However, it has been possible to determine that additionally occurring effects in a device, which includes at least one first pump cell, one reference cell, and one second pump cell and which is configured for carrying out the present method, may distort the results of the detection of the portion of the measuring gas component to be detected, in particular the nitrogen oxides $NO_x$, the sulfur oxides $SO_x$, and/or the carbon oxides $CO_x$.

As described above, the oxygen which is generated from the reduction or decomposition of the measuring gas component and which preferably originates from the reduction of the nitrogen oxides $NO_x$, the sulfur oxides $SO_x$, and/or the carbon oxides $CO_x$ is transported into the reference gas chamber with the aid of the second pump current in order to detect the portion of the measuring component, using a value to which the second pump current is set. However, in addition to this oxygen ion flow, whose oxygen ions originate from the reduction of the measuring gas component containing the bound oxygen, a further oxygen ion flow based on the oxygen ion flow which is formed from oxygen ions in the first pump cell from the molecular oxygen and which are transported into the reference gas chamber via the measuring gas chamber likewise opens into the reference gas chamber. The behavior of the oxygen ion flows in question is generally such that at a low concentration of the measuring gas component containing the bound oxygen, the oxygen ion flow that originates from the first pump cell dominates, while at a high concentration of the measuring gas component containing the bound oxygen, the oxygen ion flow that is generated by reduction of the measuring gas component exceeds the oxygen ion flow originating from the first pump cell by a factor of approximately three.

Corresponding to a composition of the two oxygen ion flows, the oxygen ion concentration in the reference gas chamber changes in such a way that the above-mentioned assumption does not fully apply in practice. Since air is able to escape from the reference gas chamber along the electrode terminals, the reference cell remains unaffected by a change in the oxygen ion concentration; in particular, there is no risk of impaired functioning of the reference cell or even destruction thereof. However, the described change in the oxygen ion concentration in the reference gas chamber results in a shift of the working point of the reference cell. Due to the above-mentioned assumption, which in practice is only approximately correct, that the portion of oxygen contained in the reference gas chamber originates entirely from the reduction of the measuring gas component to be detected, the described change in the oxygen ion concentration in the reference gas chamber may thus have an influence on the accuracy of the determination in question.

Therefore, a method for detecting at least a portion of a measuring gas component containing bound oxygen in a gas mixture is provided, in which a portion of oxygen that is generated by a reduction of the measuring gas component containing the bound oxygen is detected in the presence of molecular oxygen. Nitrogen oxides $NO_x$, sulfur oxides $SO_x$, and/or carbon oxides $CO_x$, which in addition to the chemically bound oxygen O also include a portion of nitrogen N, sulfur S, and/or carbon C, respectively, are primarily used as the measuring gas component containing bound oxygen. However, in principle the present method is suitable for any measuring gas component that contains bound oxygen, preferably chemically bound oxygen, provided that at least a portion of the bound oxygen may be separated from the measuring gas component and determined in the separate form by a reduction with the aid of a catalyst that is suitable for this purpose, and which preferably is disposed in at least one controllable electrode.

In one preferred embodiment, the measuring gas component containing the bound oxygen is contained in an exhaust gas of an internal combustion engine, in particular in the automotive field.

However, in practice the gas mixture, in addition to the measuring gas component containing the bound oxygen which is separated due to its reduction from the measuring gas component, also includes molecular oxygen $O_2$, which is present in a customary terrestrial atmosphere in a considerable amount. For this reason it is therefore necessary to carry out the method in a device which is configured for initially removing the molecular oxygen, present in the gas mixture, from the gas mixture before oxygen is likewise generated therefrom by a reduction of the measuring gas component, in particular in order to thus be able to carry out the detection of the portion of the measuring gas component in the gas mixture preferably uninfluenced by the additional component of molecular oxygen.

For this purpose, a device is used which includes at least one first pump cell, one reference cell, and one second pump cell. A "pump cell" is understood to mean a chamber which includes a solid-state electrolyte that is conductive for oxygen ions at least at elevated temperatures, at least two electrodes being provided with which a potential difference across the solid-state electrolyte may be formed, and/or with which an oxygen ion flow across the solid-state electrolyte may be brought about by applying a pump current.

The present method includes steps a) through e), whereby at least some of these steps may be carried out in succession and/or concurrently, at least in part. In addition, carrying out further steps, which may or may not be described in the present patent application, is likewise possible. According to step a), a first pump current is generated in the first pump cell in such a way that a first portion of oxygen ions, which forms from the molecular oxygen that is present in the gas mixture in addition to the measuring gas component containing the bound oxygen, is transported between the measuring gas chamber and the surroundings of the device. Since the first pump cellin particular has a design as described above, the first pump current may be set to a first value in order to bring the desired first portion of oxygen ions into the measuring gas chamber via the solid-state electrolyte of the first pump cell.

According to step b), a reference pump current is applied to the reference cell, which may also be referred to as a Nernst cell, in such a way that a second portion of the oxygen ions, present in the measuring gas chamber or in the surroundings of the device, is transported into the reference gas chamber. In particular, the value of the reference pump current is set in such a way that a fixed portion of the oxygen ions forms in the reference gas chamber. For this purpose, the value of the first pump current may be appropriately set in order to also establish a fixed ratio between the first portion of the oxygen ions in the first pump cell and the second portion of the oxygen ions in the reference gas chamber.

The pump cell and reference cell used in method steps a) and b) together form the so-called "oxygen part" of the present device for detecting the portion of the measuring gas component containing the bound oxygen in the presence of molecular oxygen, the use of which allows in particular the portion of the molecular oxygen in the gas mixture to be detected. The portion of the measuring gas component containing the bound oxygen, in particular nitrogen oxides $NO_x$, remains essentially uninfluenced by the first pump current and reference pump current applied during steps a) and b), and thus arrives in the second pump cell, in which according to step c) the measuring gas component containing the bound oxygen is decomposed by catalysis in such a way that further oxygen ions are thus generated from the oxygen that was previously bound in the measuring gas component. In this regard, the decomposition of the measuring gas component containing the bound oxygen preferably takes place due to a catalytic action at at least one of the electrodes that are present at the second pump cell. In the event that the measuring gas component containing the bound oxygen includes nitrogen oxides $NO_x$, the electrodes, which are present at the second pump cell, preferably completely decompose the nitrogen oxides $NO_x$ into molecular oxygen $O_2$ and molecular nitrogen $N_2$. The molecular nitrogen $N_2$ generated in this way diffuses out of the present device without significant hindrance, while according to step d), by applying a second pump current to the second pump cell, a portion of further oxygen ions, which are formed from the additional molecular oxygen, is transported into the reference gas Chamber. This consideration accordingly applies also for the case that the measuring gas component containing the bound oxygen includes sulfur oxides $SO_x$ and/or carbon oxides $CO_x$ from which, in addition to the molecular oxygen $O_2$, a portion of molecular sulfur S and/or carbon C is generated which is removed from the present device with the aid of a suitable unit. In the related art, under the assumption described above, the portion of the measuring gas component containing the bound oxygen is generally ascertained from a value of the second pump current.

In particular, to avoid distortion of the portion of the measuring gas component to be detected, in particular the nitrogen oxides $NO_x$, the sulfur oxides $SO_x$, and/or the carbon oxides $CO_x$, due to the error sources described above, according to step e) a sum of currents that is formed from the reference pump current and the second pump current is held constant. Holding a sum of currents constant is understood to mean a procedure according to which the value of the sum of the currents remains within a fixed range that is above a fixed minimum threshold and below a fixed maximum threshold. By thus preferably controlling the value of the reference pump current in order to meet the condition of constancy of the two currents according to step e), it is thus possible to now determine the portion of the measuring gas component containing the bound oxygen based on the value of the second pump current. Since the influence of the oxygen ion flow described above, which enters from the first pump cell into the reference gas chamber, may be excluded in this way, it is thus possible in particular to increase the accuracy of the detection of the portion of the measuring gas component containing the bound oxygen.

In another aspect, the present invention includes a computer program which is configured for carrying out the steps of the described method.

In another aspect, the present invention includes an electronic memory medium which is configured for storing a computer program equipped in this way.

In another aspect, the present invention includes an electronic control unit which includes at least one unit for detecting, for setting, and/or for regulating in each case a value of the first pump current, the reference pump current, and/or the second pump current. In one preferred embodiment, the electronic control unit includes at least one electronic memory medium on which a computer program, which is configured for carrying out the steps of the described method, is stored. It is irrelevant whether the electronic control unit according to the present invention has a one-part or multi-part design, i.e., whether the electronic memory medium and the at least one unit are present in the form of a single device or in the form of one or multiple separate devices.

In one particularly preferred embodiment, it is advantageous to subdivide the at least one unit into three, actually or only notionally, separate parts, in particular a first unit for detecting the value of the reference pump current;

a second unit for setting the value of the reference pump current; and a third unit for regulating the value of the reference pump current.

In this regard, in particular the first unit for detecting the value of the reference pump current and the second unit for setting the value of the reference pump current may be designed as separate units, or also combined in the form of a single unit.

In one preferred embodiment, the first unit for detecting the value of the reference pump current includes at least one measuring shunt which is provided for detecting the value of the reference pump current. In this way, the first unit may be used for measuring a variable of the reference pump current or an electrical signal proportional thereto. As explained in greater detail in the exemplary embodiments, the measuring shunt may preferably be selected from a resistance for determining the reference pump current;
a resistance for determining the second pump current;
a resistance that is introduced into an electrically conductive connection of the electronic control unit to a reference electrode of the reference cell; or
an internal resistance of an analog-digital converter that is introduced into the electronic control unit.

In one preferred embodiment, the second unit for setting the value of the reference pump current includes at least one adjustable current source. The term "current source" is understood to mean an electronic unit having at least one input for receiving a control signal, at least one unit for generating a current signal, and at least one output for delivering the current signal, whereby with the aid of the control signal, a magnitude of the current and/or a direction of the current, preferably both the magnitude of the current and the direction of the current, may be established. The adjustable current source may have either a voltage-controlled or a current-controlled design; i.e., in the case of the voltage-controlled current source, the control signal is a voltage signal, while in the case of the current-controlled current source, the control signal represents a current signal.

In one particular embodiment, the second unit for setting the value of the reference pump current may have two separate, independently adjustable current sources which are interconnected in such a way that the two separately adjustable current sources have opposite potential references. In this way, the second unit may reverse the value of the reference pump current, and thus provide the value of the reference pump current in a first current direction, and also in a second current direction having an algebraic sign opposite that of the first current direction.

In one particularly preferred embodiment, the third unit for regulating the value of the reference pump current is designed in such a way that the third unit provides the input signal for the at least one adjustable current source, which is used as a controller manipulated variable. The value of the reference pump current, which is provided in particular by the first unit for detecting the value of the reference pump current, and a reference variable and/or a control variable for the value of the reference pump current may preferably be used as input variables for the third unit for regulating the value of the reference pump current.

The electronic control unit having the design described here has numerous advantages, in particular with regard to an improvement in the accuracy of detection of the measuring gas component, in particular the nitrogen oxides, in the gas mixture, an improvement in the dynamic behavior of the present device, and increased options for carrying out the on-board diagnostics (OBD) of a motor vehicle equipped with the present device.

When the output current of the at least one adjustable current source can be precisely set and determined, it may thus be possible to compensate for any variations in the adjustable current source that may occur. The oxygen partial pressure in the reference cell may be appropriately controlled with the aid of the settable value of the reference pump current. In this way, a transfer function of a controlled system, which is controlled by the third unit for regulating the value of the reference pump current, may be influenced and appropriately adapted. In addition, an influence of the second pump current, which is a function of the portion of the measuring gas component containing the bound oxygen in the gas mixture, on the oxygen partial pressure in the reference cell may thus likewise be compensated for. Furthermore, accurately detecting the value of the reference pump current may make it possible to precisely pinpoint malfunctions of components of the present sensor element.

In another aspect, the present invention includes a device for detecting the at least one portion of the measuring gas component containing the bound oxygen in the gas mixture, in particular in the exhaust gas of the internal combustion engine, whereby that portion of oxygen that is generated by the reduction of the measuring gas component containing the bound oxygen is detected in the measuring gas chamber when molecular oxygen is present in the device. The device includes at least one first pump cell, at least one reference cell, at least one second pump cell, and at least one electronic control unit described herein. For further particulars with regard to the stated components of the device, reference is made to the description of the method and/or to the description of the electronic control unit.

DETAILED DESCRIPTION

Figure 1:
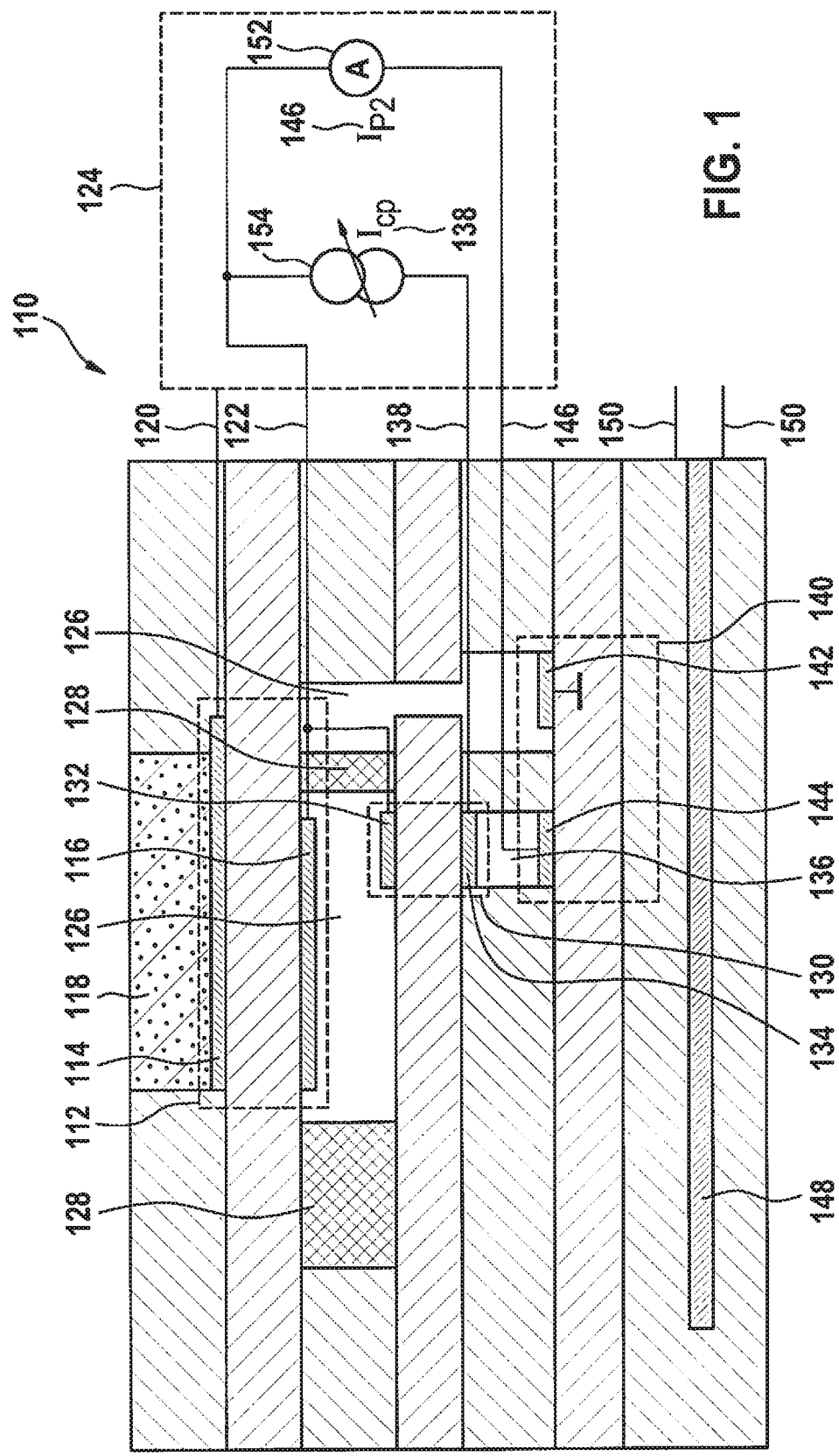
FIG. 1 shows one preferred exemplary embodiment of the present method, using a particularly advantageous device for detecting at least a portion of a measuring gas component containing bound oxygen.

FIG. 1 illustrates one preferred exemplary embodiment of the present method, using a particularly advantageous device 110 for detecting at least a portion of a measuring gas component containing bound oxygen, referred to below by way of example as nitrogen oxides $NO_x$, in a gas mixture, for example an exhaust gas of an internal combustion engine.

Device 110 includes a first pump cell 112 which is provided between an outer pump electrode 114 and an inner pump electrode 116. Outer pump electrode 114, which is separated from the surroundings of device 110 with the aid of a porous aluminum oxide layer 118, has a first electrically conducting connection via which a first pump current 120 may be generated in first pump cell 112. To obtain a complete circuit, inner pump electrode 116 likewise has an electrically conducting connection which leads to a shared terminal 122 of an external electronic control unit 124. By generating first pump current 120 in first pump cell 112, a first portion of oxygen ions that is formed from molecular oxygen from the gas mixture may be transported between a measuring gas chamber 126 and the surroundings of device 110. Two diffusion barriers 128 are present in the entry path from the surroundings to measuring gas chamber 126, which in the present case is designed in the form of two separate cavities.

The device also includes a reference cell 130, which is adjoined by a Nernst electrode 132 and a reference electrode 134. While Nernst electrode 132 together with inner pump electrode 116 has an electrically conducting connection to shared terminal 122, reference electrode 134 has an electrically conducting connection to a supply voltage. A second portion of the oxygen ions from measuring gas chamber 126 and/or from the surroundings of device 110 is transported into a reference gas chamber 136 by applying a reference pump current 138 between the supply voltage and shared terminal 122. The value of reference pump current 138 is hereby set in such a way that a fixed portion of the oxygen ions forms in reference gas chamber 136. In this regard, in addition the value of first pump current 120 is preferably set in such a way that a fixed ratio between the first portion of the oxygen ions in the measuring gas chamber and the second portion of the oxygen ions in reference gas chamber 136 results.

The measuring gas component nitrogen oxides $NO_x$, containing the bound oxygen and likewise contained in the gas mixture, enters, in particular by diffusion, second pump cell 140, also referred to as "$NO_x$ pump cell," largely uninfluenced. Second pump cell 140 is adjoined by a $NO_x$ pump electrode 142 and a $NO_x$ counter electrode 144. At least one of the two electrodes, $NO_x$ pump electrode 142 and/or $NO_x$ counter electrode 144, is designed in such a way that when a voltage is applied by catalysis, additional molecular oxygen may be generated from the measuring gas component $NO_x$, and is formed in second pump cell 140.

While $NO_x$ pump electrode 142 has an electrically conducting connection that leads to sharedterminal 122, $NO_x$ counter electrode 144 has an electrically conducting connection via which a second pump current 146 may be applied to second pump cell 140. When a second pump current 146 is applied to second pump cell 140, a portion of further oxygen ions that have been formed from the additional molecular oxygen is transported into reference gas chamber 136.

Device 110 also includes a heating element 148 which has a heating line 150 via which a heating current may be introduced into heating element 148, which is able to bring device 110 to the desired temperature by generating heating power.

For carrying out the present method for detecting the portion of a measuring gas component containing bound oxygen in a gas mixture, electronic control unit 124 includes a measuring device 152 for determining the value of second pump current 146, and includes a regulator 152 with the aid of which the value of reference pump current 138 may be regulated in such a way that a sum of currents that is formed from reference pump current 138 and second pump current 146 may be held constant. Further components which may be included in electronic control unit 124 are not illustrated in FIG. 1 for reasons of clarity.

Holding a sum of currents constant is understood to mean a procedure according to which the value of the sum of the currents remains within a fixed range that is above a fixed minimum threshold and below a fixed maximum threshold. In this way, fluctuations that occur in device 110, which cannot be completely prevented despite all technical measures, may still be taken into account.

Figure 2:
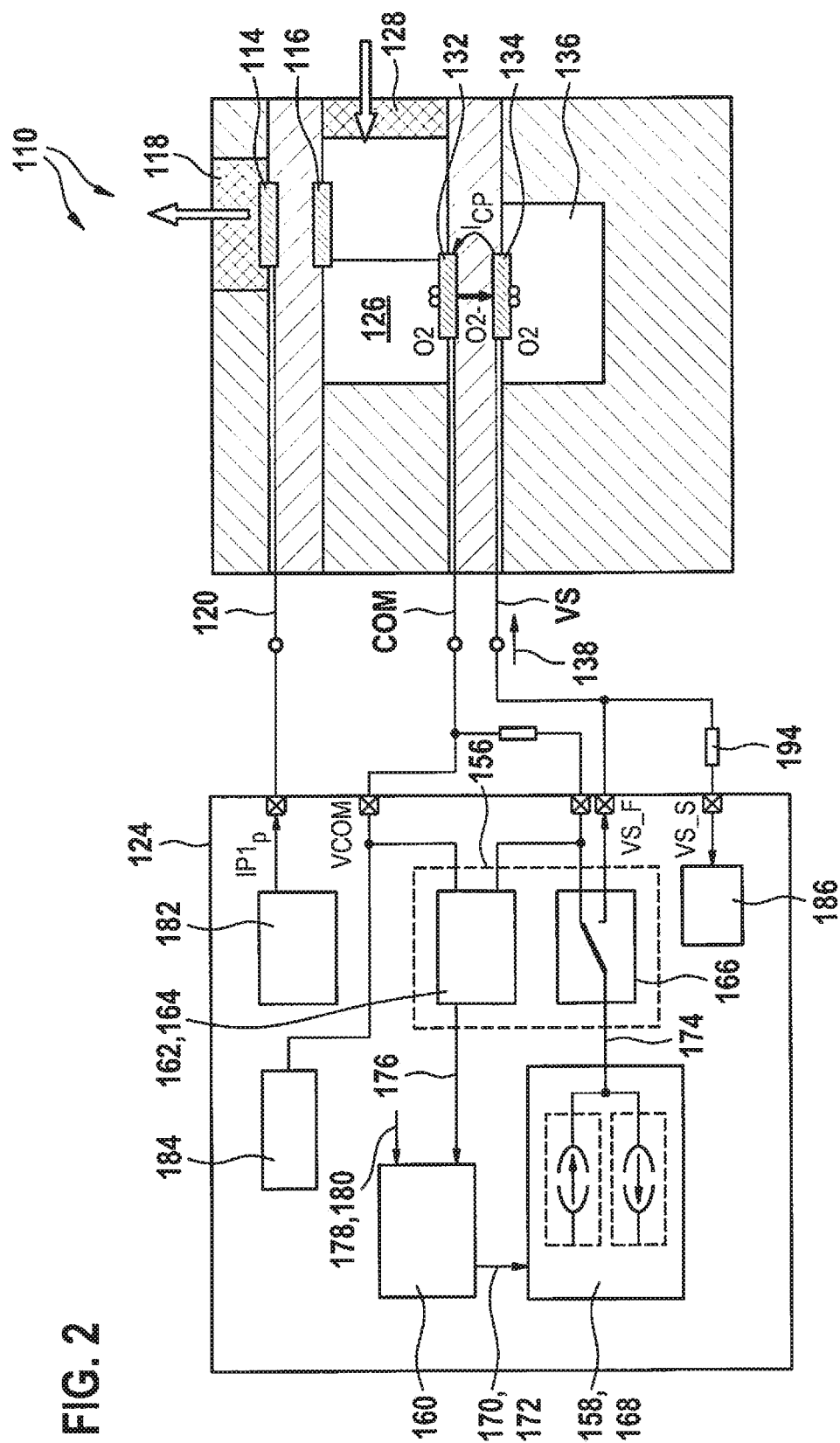
FIG. 2 shows one particularly preferred exemplary embodiment of an electronic control unit for the device for detecting the portion of the measuring gas component containing the bound oxygen.

FIG. 2 illustrates one particularly preferred exemplary embodiment of electronic control unit 124 for use in present device 110 for detecting the portion of the measuring gas component containing the bound oxygen. Electronic control unit 124 includes a circuit 156 for detecting the value of reference pump current 138, an adjustable current source 158, and a regulator 160 for regulating the value of reference pump current 138.

In the exemplary embodiment illustrated in FIG. 2, circuit 156 for detecting the value of reference pump current 138 includes an analog-digital converter 162 which has an internal resistance 164 that is detectable depending on the selection of a setting of a switch 166. Internal resistance 164 of analog-digital converter 162 is employed as a measuring shunt which may be used for detecting the value of reference pump current 138. Further embodiments are possible, and are described in the exemplary embodiments below.

In the exemplary embodiment according to FIG. 2, adjustable current source 158 for setting the value of reference pump current 138 is designed as a configurable current source 168 having a reversible polarity. Adjustable current source 158 hereby receives as input signal 170 a manipulated variable 172 that is provided by regulator 160. In the present exemplary embodiment, output signal 174 of adjustable current source 158 is supplied to switch 166, and, depending on the setting of switch 166, is provided as reference pump current 138 to reference electrode 134 or used for determining internal resistance 164 of analog-digital converter 162.

Regulator 160, which provides manipulated variable 172 for controlling input signal 170 of adjustable current source 158, receives as first input variable 176 the value of reference pump current 138 detected by circuit 156. A predefined reference value 180 is provided as second input variable 178 of regulator 160.

Electronic control unit 124, illustrated by way of example in FIG. 2, also includes a second adjustable current source 182 for providing a value of first pump current 120, via a voltage source 184 for providing a shared potential for reference cell 130 and via a second analog-digital converter 186 for detecting a value of the Nernst voltage.

Various embodiments of circuit 156 for detecting the value of reference pump current 138 are illustrated in subsequent FIGS. 3 through 6. Reference is made to the above description of FIG. 2 for details not mentioned in the following description of FIGS. 3 through 6.

Figure 3:
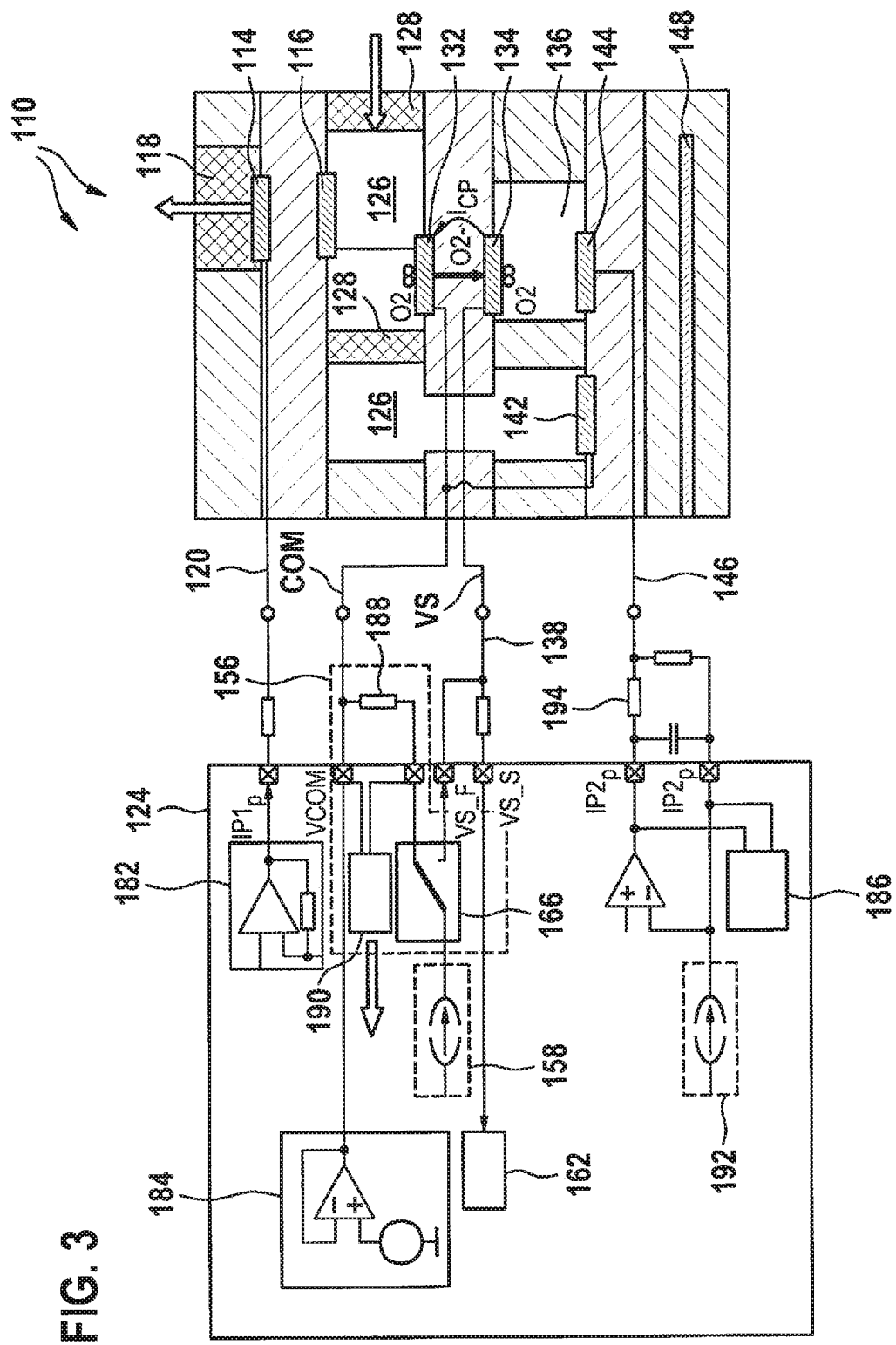
FIG. 3 shows a first exemplary embodiment of a circuit for detecting a value of a reference pump current.

In the exemplary embodiment according to FIG. 3, circuit 156 for detecting the value of reference pump current 138 includes an additional measuring shunt 188, which according to illustrated circuit 156 is used for determining the value of the reference pump current. The current provided by adjustable current source 158 is initially supplied to switch 166, which, depending on the setting of switch 166, conducts reference pump current 138 to reference electrode 134 or relays it to additional high-resistance measuring shunt 188. The latter may advantageously take place in particular in an operating phase in which applying reference pump current 138 to the sensor element is not necessary, for example at the beginning of the start phase. The value of reference pump current 138 is ascertained with the aid of an additional analog-digital converter 190. Electronic control unit 124 illustrated in FIG. 3 also includes a third adjustable current source 192 for generating second pump current 146.

Figure 4:
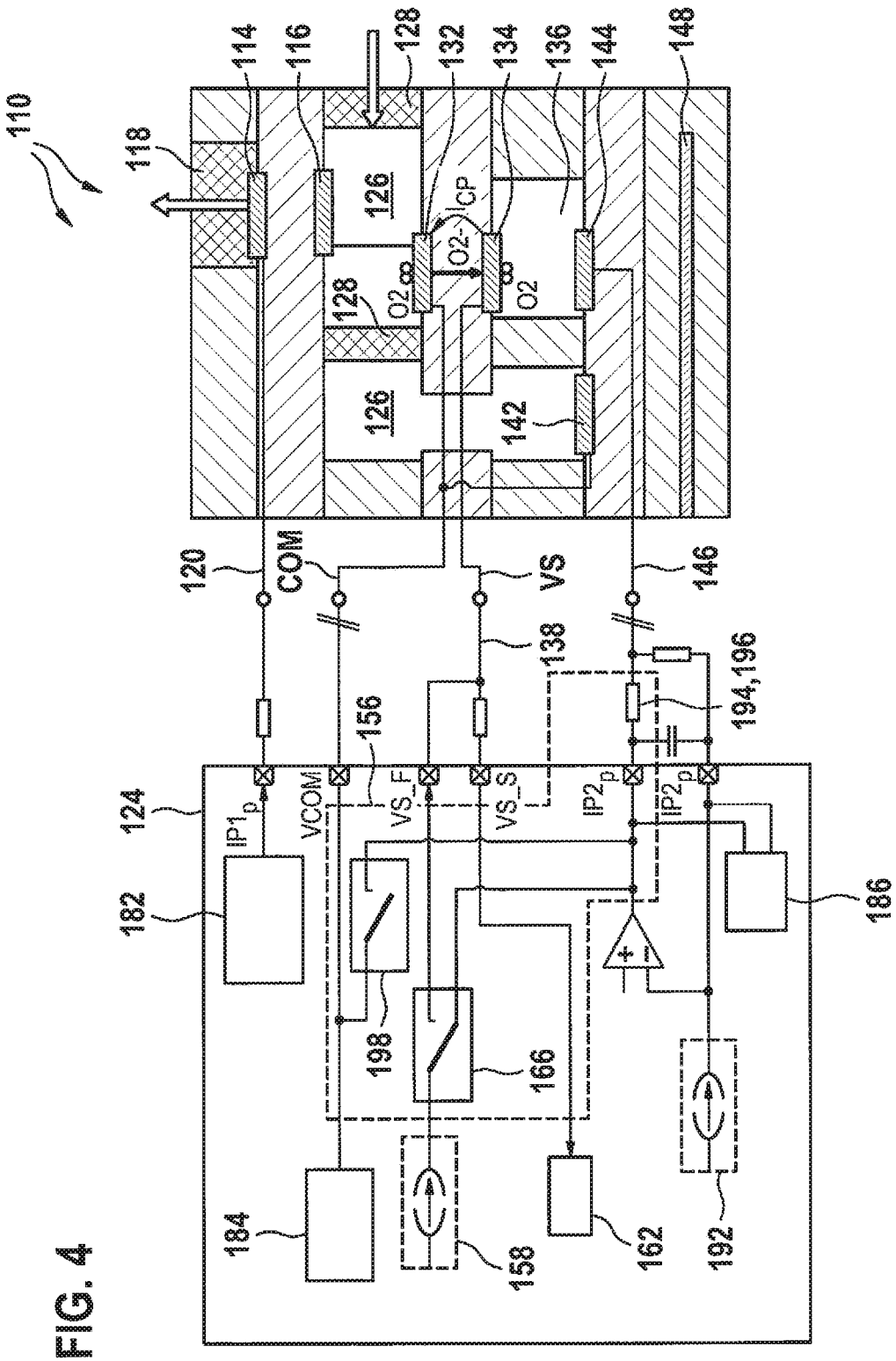
FIG. 4 shows a second exemplary embodiment of the circuit for detecting the value of the reference pump current.

FIG. 4 illustrates another exemplary embodiment for circuit 156 for detecting the value of reference pump current 138. In this exemplary embodiment, a measuring shunt 194, present in electronic control unit 124, for detecting a value of second pump current 146 is used as measuring shunt 196 for detecting the value of reference pump current 138. In an operating state in which the sensor element is not active and therefore has a very high resistance, with the aid of switch 166 and an additional switch 198 the value of reference pump current 138 may be switched to measuring shunt 194 for determining the second pump current 146 in order to determine the value of reference pump current 138 with the aid of second analog-digital converter 186.

Figure 5:
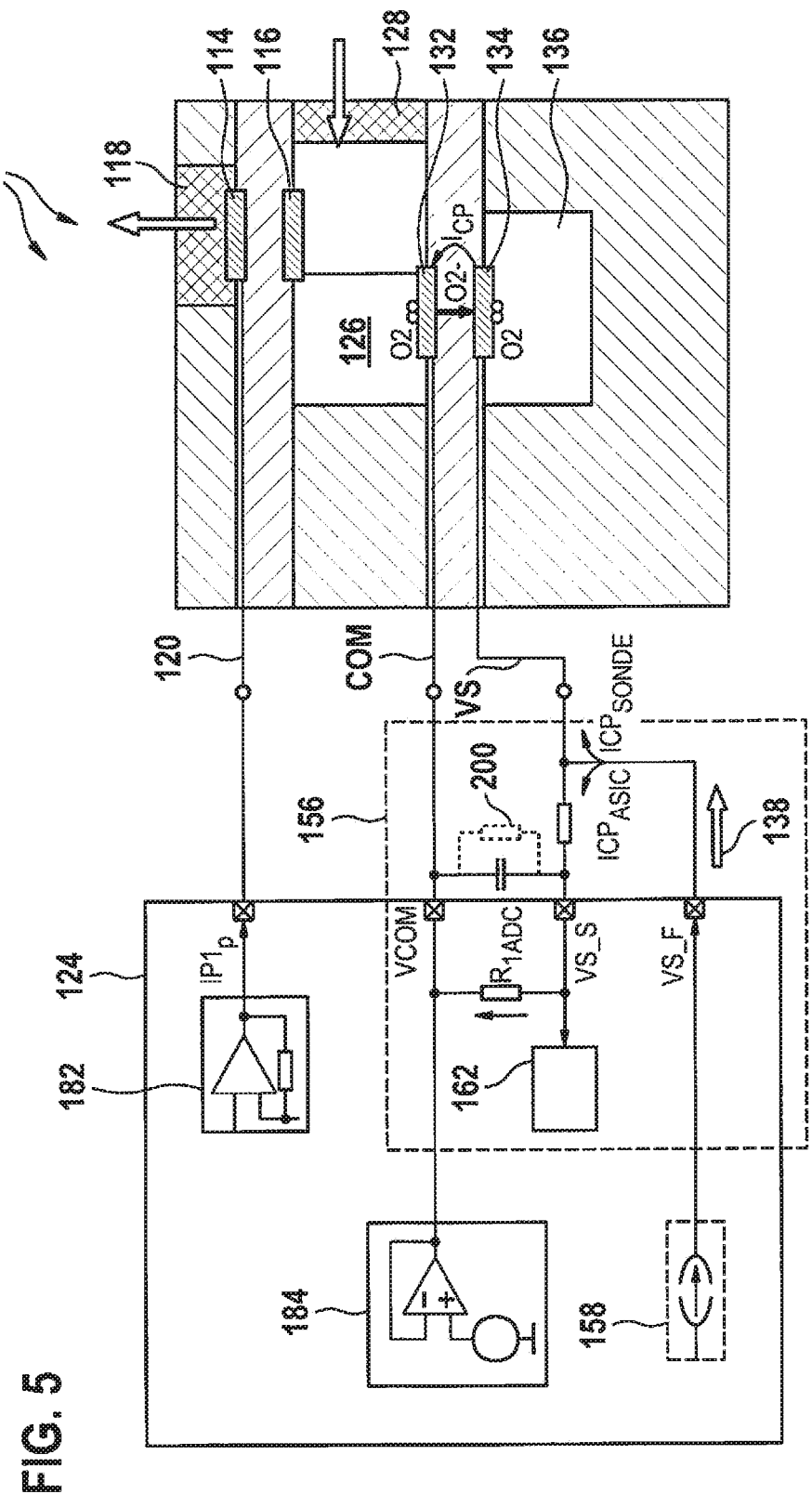
FIG. 5 shows a third exemplary embodiment of the circuit for detecting the value of the reference pump current.

In the exemplary embodiment according to FIG. 5, an observation from actual practice is taken into account, in that all of the current that is generated by adjustable current source 158 often does not reach the sensor element, since a portion of the current takes a different path to virtual ground COM, and, for example, flows through analog-digital converter 162, which has an internal resistance. In addition, parasitic resistances of capacitors, schematically illustrated in FIG. 5 by resistor 200, may also reduce the value of reference pump current 138.

Figure 6:
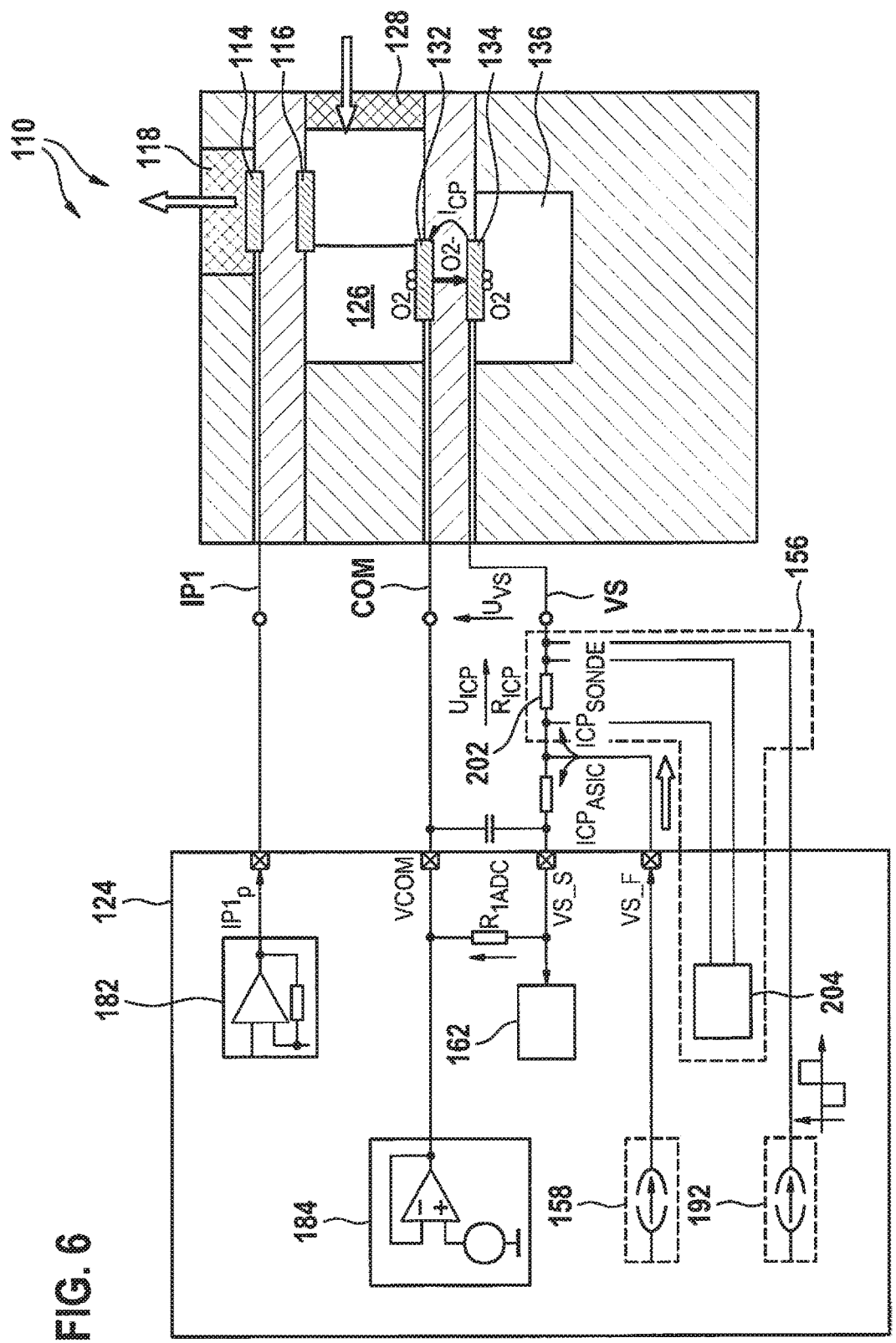
FIG. 6 shows a fourth exemplary embodiment of the circuit for detecting the value o the reference pump current.

As schematically illustrated in FIG. 6, it is therefore provided to introduce a further additional measuring shunt 202 into the Vs line from electronic control unit 124 to the sensor element, and via the voltage drop that occurs at further additional measuring shunt 202, to determine the value of reference pump current 138 which arrives at reference electrode 134 in the sensor element. In particular, an additional analog-digital converter 204 may be used for this purpose. Since the value of voltage Vs is influenced by the voltage drop at additional measuring shunt 202, the voltage drop that occurs at the additional measuring shunt is preferably added to the detected value of voltage Vs in order to compensate for the change in the measured value of voltage Vs.

Another exemplary embodiment for detecting the value of reference pump current 138 may also be found in FIG. 3 above. As described there, reference pump current 138 may be determined via the voltage drop across additional measuring shunt 188. Since internal resistance 164 of analog-digital converter 162 is generally detected and stored, together with further calibration data for analog-digital converter 162, in a memory, with knowledge of the internal resistance of analog-digital converter 162, the actual current flowing through analog-digital converter 162 may be computed, since voltage Vs at analog-digital converter 162 is also detected. In an operating mode in which analog-digital converter 162 takes a measurement only during certain phases, so that current flows through internal resistance 164 of analog-digital converter 162 also only during these phases, the percentage of the loss of reference pump current 138 may be ascertained by proportionally relating the current flowing through analog-digital converter 138 to an entire period duration.

Figure 7:
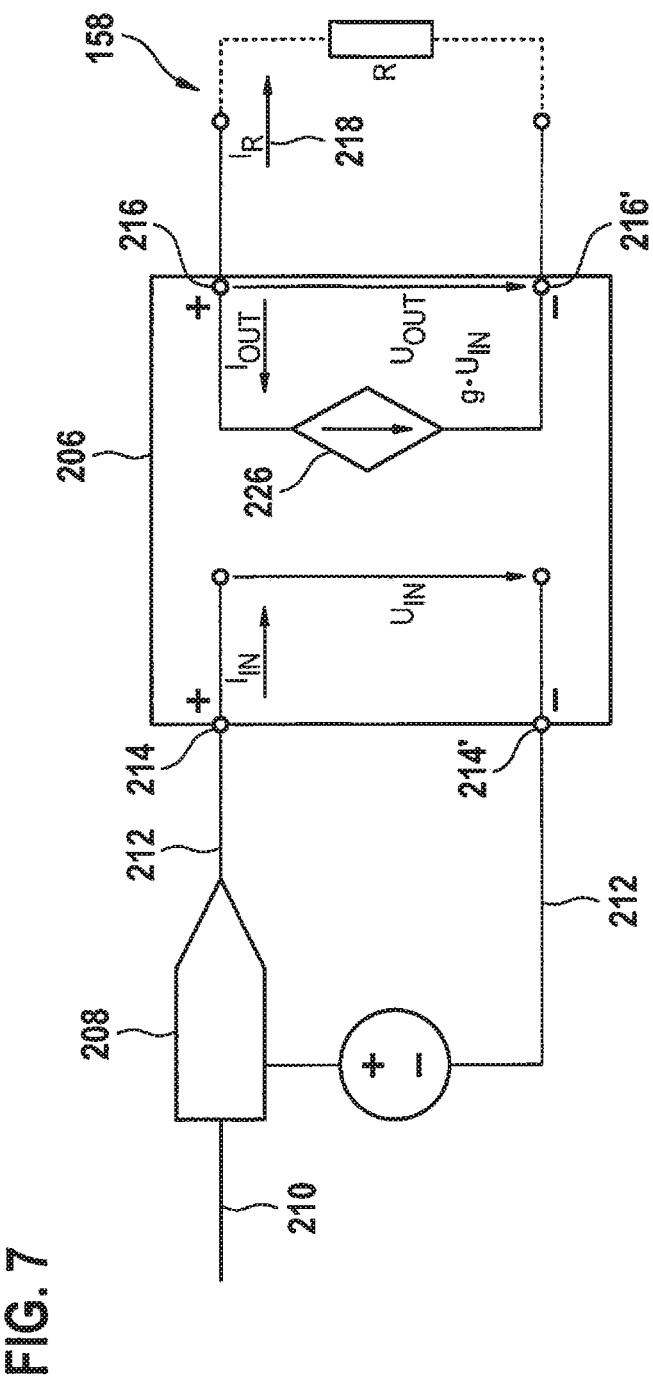
FIG. 7 shows one exemplary embodiment of a voltage-controlled current source for setting a value of the reference pump current.
Figure 8:
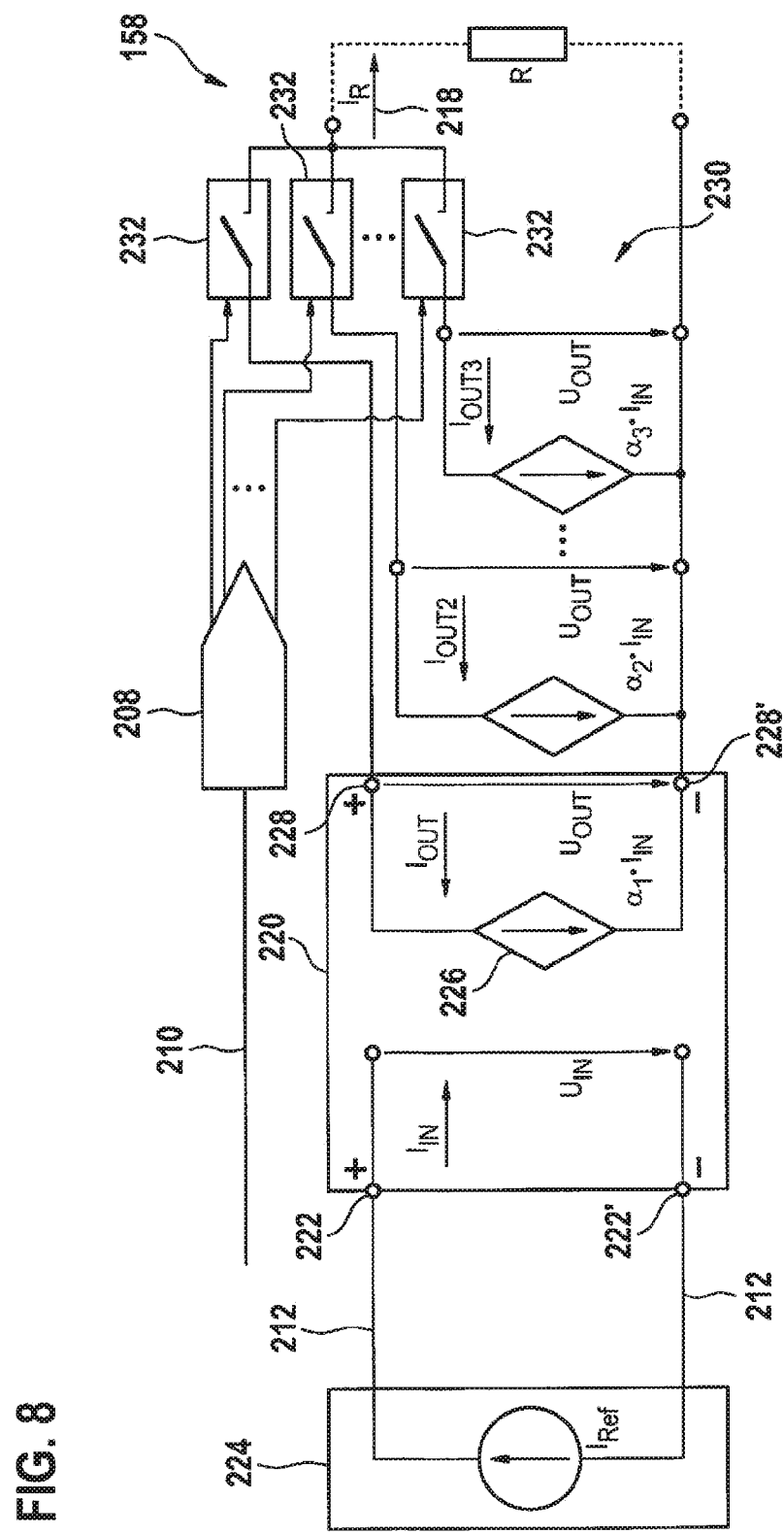
FIG. 8 shows one exemplary embodiment of a current-controlled current source for setting the value of the reference pump current.
Figure 9:
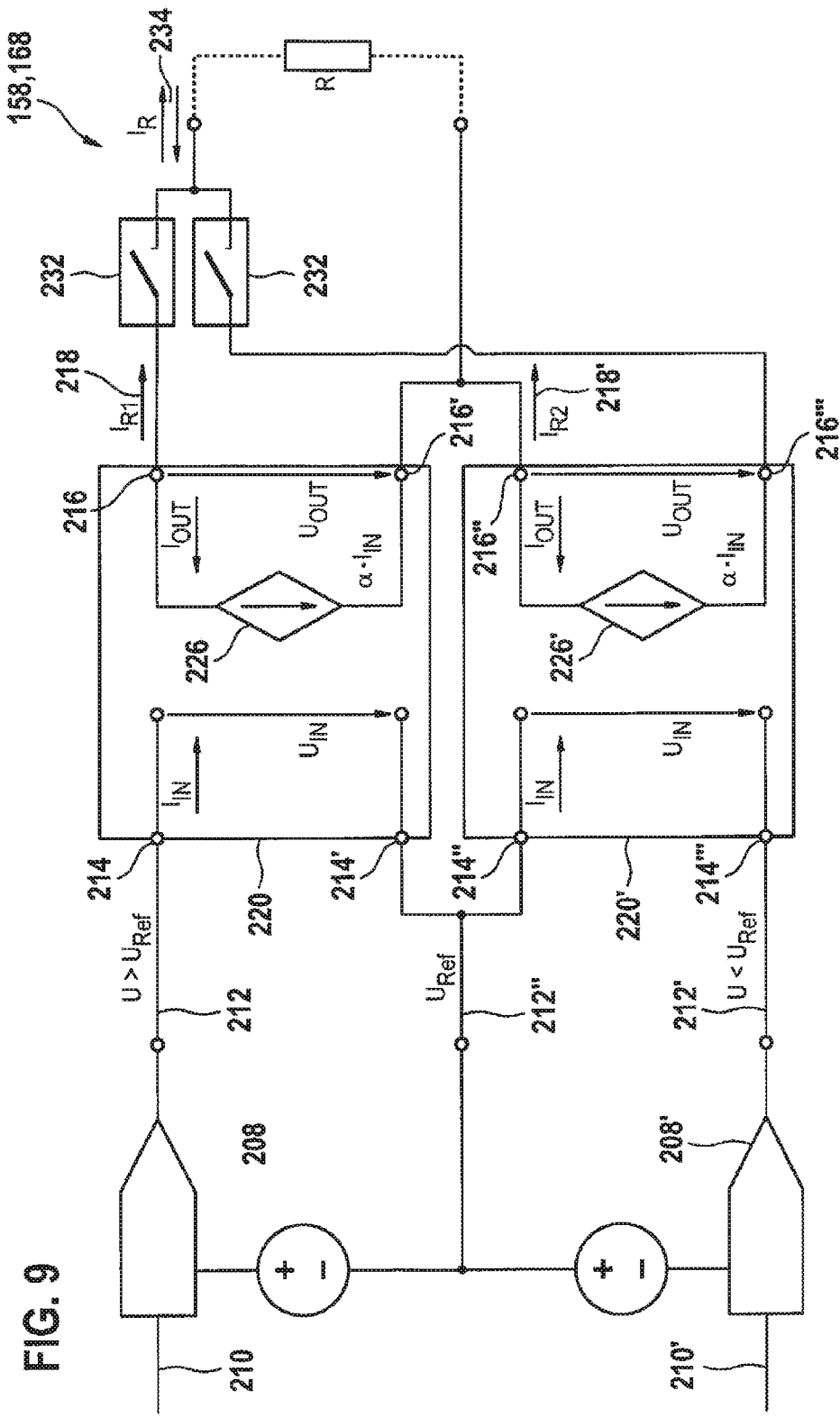
FIG. 9 shows one exemplary embodiment of a bipolar current-controlled current source for setting a value having an arbitrary algebraic sign for the reference pump current.

Preferred exemplary embodiments of one embodiment of adjustable current source 158, which electronic control unit 124 may include for setting the value of reference pump current 138, are illustrated in subsequent FIGS. 7 through 9.

In a first exemplary embodiment of adjustable current source 158, FIG. 7 schematically illustrates a voltage-controlled current source 206 in the form of an equivalent circuit diagram. In this example, an n-bit digital-analog converter 208 generates a voltage signal 212 from an n-bit control word 210. Voltage control signal 212, present at input 214, 214' of voltage-controlled current source 206, thus generates at output 216, 216' of voltage-controlled current source 206 a current 218 having a magnitude that is adjustable via voltage control signal 212.

FIG. 8 schematically illustrates another exemplary embodiment in the form of an equivalent circuit diagram of a current-controlled current source 220. in this exemplary embodiment, a so-called "current mirror" is used which converts an input current from a reference current source 224 into a voltage. This voltage in turn controls an internal current source 226 which sets the value of the current at outputs 228, 228' of current-controlled current source 220. A so-called "gain" of the current mirror describes a ratio of the value of the output current to the value of the particular input current. Since the output currents may be summed due to line connections 230, switching the current mirror with a different gain in each case allows an output current to be set to a certain value. Setting of the value of output current 218 may take place by use of switches 232, whose control, as described above, here as well may take place by n-bit digital-analog converter 208, which is controlled with the aid of an n-bit control word 210.

FIG. 9 shows that configurable current source 168, which includes two adjustable current-controlled current sources 220, 220', may be interconnected in such a way that the direction of the current flow may be reversed. The two n-bit digital-analog converters 208, 208' in each case convert incoming n-bit control word 210, 210' into voltage control signals 212, 212', 212" at inputs 214, 214' of first current-controlled current source 220, and at inputs 214", 214'" of second current-controlled current source 220' into a voltage in each case which operates a current source 226, 226', respectively, associated current source 226, 226' determining respective current 218, 218' at outputs 216, 216', 216", 216'. By use of switches 232, the two currents 218, 218' may be added in such a way that an overall current 234, which may have an arbitrary direction, may be generated.

Figure 10:
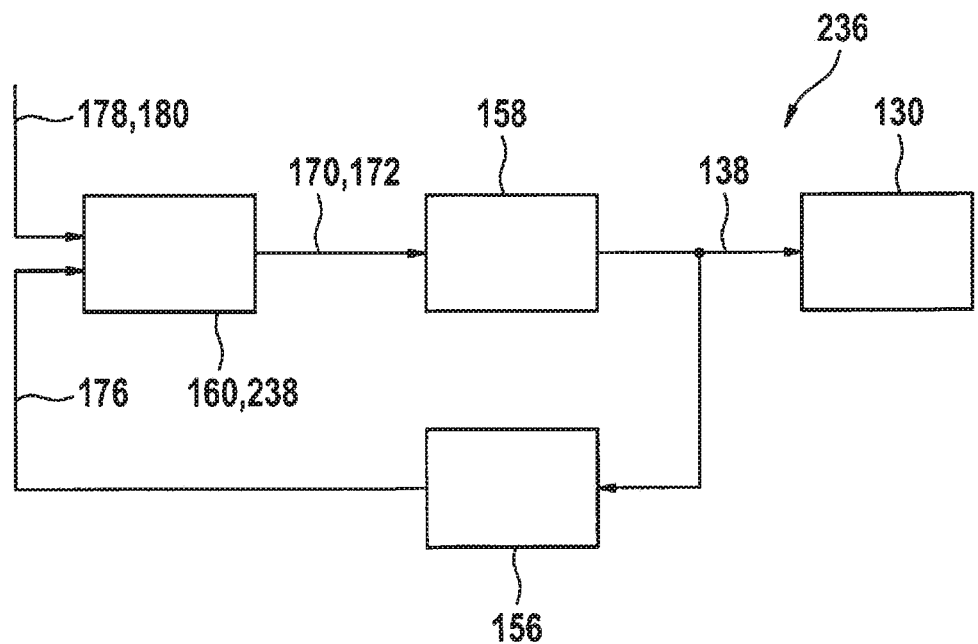
FIG. 10 shows one exemplary embodiment of a unit for regulating the value of the reference pump current.

FIG. 10 schematically shows a control circuit 236 for reference pump current 138 of reference cell 130. Control circuit 236 is formed from controllable current source 158, circuit 156 for detecting the value of reference pump current 138, and regulator 160. Manipulated variable 172, which forms input signal 170 for controllable current source 158, may be formed from the measured value of reference pump current 138 as first input variable 176, and reference value 180 or the control variable as second input variable 178 with the aid of a digital or analog circuit.

Figure 11:
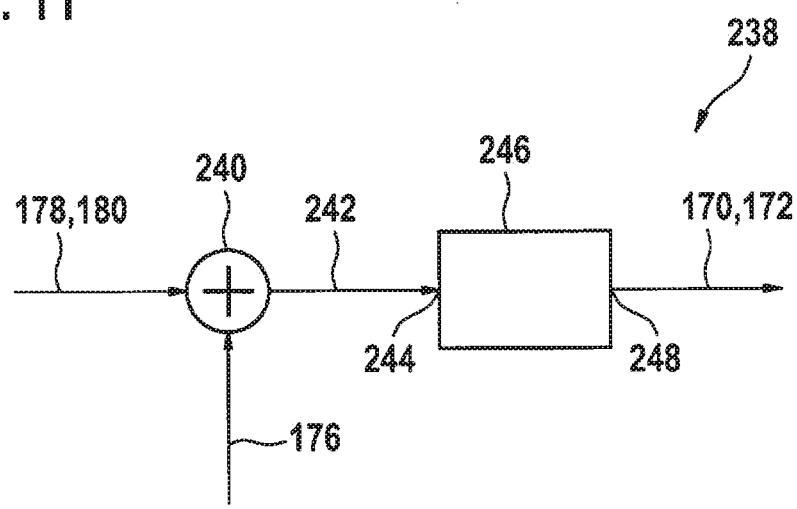
FIG. 11 shows one exemplary embodiment for implementing the regulation of the value of the reference pump current.

Regulator 160 may preferably have a control algorithm 238, whose implementation is schematically illustrated in FIG. 11. By comparing the value of reference pump current 138 to reference value 180, with reference pump current 138 being used as first input variable 176 and reference value 180 as second input variable 178, an error signal 242 is generated in an adder 240 and is delivered to an input 244 of a digital circuit 246. Digital circuit 246 is configured in such a way that it provides manipulated variable 172, which is available as input signal 170 for controllable current source 158, to an output 248.

What is claimed is:

1. A method for detecting at least a portion of a measuring gas component containing bound oxygen in a gas mixture in a measuring gas chamber by detecting a portion of oxygen that is generated by a reduction of the measuring gas component containing the bound oxygen, in the presence of molecular oxygen, in a device, which includes at least one first pump cell, one reference cell, and one second pump cell, the method comprising:

a) generating a first pump current in the first pump cell so that transport of a first portion of oxygen ions takes place between the measuring gas chamber and surroundings of the device;

b) generating a reference pump current in the reference cell so that a second portion of the oxygen ions is transported into a reference gas chamber;

c) decomposing the measuring gas component containing the bound oxygen by catalysis at an electrode of the second pump cell, as a result of which additional molecular oxygen is generated from the measuring gas component; d) generating a second pump current to the second pump cell so that a portion of further oxygen ions that are formed from the additional molecular oxygen is transported into the reference gas chamber; and forming a sum of currents from the reference pump current and from the second pump current, wherein the sum of currents remains within a fixed range.

2. The method as recited in claim 1, wherein the measuring gas component is in an exhaust gas of an internal combustion engine.

3. The method as recited in claim 1, wherein a value of the reference pump current is set so that the sum of the currents is held within a fixed range, and wherein the portion of the measuring gas component containing the bound oxygen in the gas mixture is determined based on a value of the second pump current.

4. The method as recited in claim 1, wherein the decomposing of the measuring gas component containing the bound oxygen takes place by a catalytic action of electrodes which adjoin the second pump cell.

5. The method as recited in claim 1, wherein a value of the first pump current is set so that a fixed ratio between the first portion of the oxygen ions and the second portion of the oxygen ions results.

6. The method as recited in claim 1, wherein a value of the reference pump current is set so that a fixed portion of the oxygen ions is transported into the reference gas chamber.

7. A non-transitory electronic memory medium on which a computer program is stored, which is executable by a processor, comprising:

a program code arrangement having program code for detecting at least a portion of a measuring gas component containing bound oxygen in a gas mixture in a measuring gas chamber by detecting a portion of oxygen that is generated by a reduction of the measuring gas component containing the bound oxygen, in the presence of molecular oxygen, in a device, which includes at least one first pump cell, one reference cell, and one second pump cell, by performing the following:

a) generating a first pump current in the first pump cell so that transport of a first portion of oxygen ions takes place between the measuring gas chamber and surroundings of the device;

b) applying a reference pump current to the reference cell so that a second portion of the oxygen ions is transported into a reference gas chamber;

c) decomposing the measuring gas component containing the bound oxygen by catalysis at an electrode of the second pump cell, as a result of which additional molecular oxygen is generated from the measuring gas component;

d) applying a second pump current to the second pump cell so that a portion of further oxygen ions that are formed from the additional molecular oxygen is transported into the reference gas chamber; and forming a sum of currents from the reference pump current and from the second pump current, wherein the sum of currents remains within a fixed range.

8. An electronic control unit comprising:

at least one unit for at least one of detecting, setting, and regulating a value of at least one of a first pump current, a reference pump current, and a second pump current;

an electronic memory medium on which a computer program is stored and which is configured for detecting at least a portion of a measuring gas component containing bound oxygen in a gas mixture in a measuring gas chamber by detecting a portion of oxygen that is generated by a reduction of the measuring gas component containing the bound oxygen, in the presence of molecular oxygen, in a device, which includes at least one first pump cell, one reference cell, and one second pump cell, by performing the following:

a) generating a first pump current in the first pump cell so that transport of a first portion of oxygen ions takes place between the measuring gas chamber and surroundings of the device;

b) applying a reference pump current to the reference cell so that a second portion of the oxygen ions is transported into a reference gas chamber;

c) decomposing the measuring gas component containing the bound oxygen by catalysis at an electrode of the second pump cell, as a result of which additional molecular oxygen is generated from the measuring gas component;

d) applying a second pump current to the second pump cell so that a portion of further oxygen ions that are formed from the additional molecular oxygen is transported into the reference gas chamber; and forming a sum of currents from the reference pump current and from the second pump current, wherein the sum of currents remains within a fixed range.

9. The electronic control unit as recited in claim 8, further comprising:

a measuring shunt for detecting a value of the reference pump current, wherein the measuring shunt includes one of:

a resistance for determining the reference pump current, a resistance for determining the second pump current, a resistance that is introduced into a connection of the electronic control unit to a reference electrode of the reference cell, and an internal resistance of an analog-digital converter that is present in the electronic control unit.

10. The electronic control unit as recited in claim 9, further comprising:

at least one adjustable current source for setting the value of the reference pump current.

11. The electronic control unit as recited in claim 10, wherein the adjustable current source is one of voltage-controlled and current-controlled.

12. The electronic control unit as recited in claim 8, further comprising two separate current-controlled current sources that are interconnected so that the two current-controlled current sources have opposite potential references.

13. The electronic control unit as recited in claim 10, further comprising:

at least one regulator for regulating the value of the reference pump current, wherein:

the regulator receives at least two input variables and delivers at least one manipulated variable, the input variables include values of the reference pump current and a reference value for the regulator, and the manipulated variable is deliverable as an input signal to the adjustable current source.

14. A device for detecting at least a portion of a measuring gas component containing bound oxygen in a gas mixture in a measuring gas chamber by detecting a portion of oxygen that is generated by a reduction of the measuring gas component containing the bound oxygen, in the presence of molecular oxygen, in the device, comprising:

at least one first pump cell;
a reference cell;
a second pump cell; and
an electronic control unit, including:
at least one unit for at least one of detecting, setting, and regulating a value of at least one of a first pump current, a reference pump current, and a second pump current; and
an electronic memory medium on which a computer program is stored and which is configured for detecting at least a portion of a measuring gas component containing bound oxygen in a gas mixture in a measuring gas chamber by detecting a portion of oxygen that is generated by a reduction of the measuring gas component containing the bound oxygen, in the presence of molecular oxygen, in a device, which includes at least one first pump cell, one reference cell, and one second pump cell, by performing the following:

a) generating a first pump current in the first pump cell so that transport of a first portion of oxygen ions takes place between the measuring gas chamber and surroundings of the device;

b) applying a reference pump current to the reference cell so that a second portion of the oxygen ions is transported into a reference gas chamber;

c) decomposing the measuring gas component containing the bound oxygen by catalysis at an electrode of the second pump cell, as a result of which additional molecular oxygen is generated from the measuring gas component;

d) applying a second pump current to the second pump cell so that a portion of further oxygen ions that are formed from the additional molecular oxygen is transported into the reference gas chamber; and forming a sum of currents from the reference pump current and from the second pump current, wherein the sum of currents remains within a fixed range.

15. The device as recited in claim 14, wherein the measuring gas component is in an exhaust gas of an internal combustion engine.

* * * * *